US009408794B2

(12) United States Patent
Lewus et al.

(10) Patent No.: US 9,408,794 B2
(45) Date of Patent: Aug. 9, 2016

(54) ORAL CARE PRODUCT AND METHODS OF USE AND MANUFACTURE THEREOF

(75) Inventors: Catherine Lewus, Denville, NJ (US); Gregory Szewczyk, Flemington, NJ (US); Sarita Mello, North Brunswick, NJ (US); Kimdra Smith-Webster, Williamstown, NJ (US); Jason Nesta, Cedar Knolls, NJ (US); Rensl Dillon, Ewing, NJ (US); Evangelia S. Arvanitidou, Princeton, NJ (US); Christine Cuiule, Mount Laurel, NJ (US)

(73) Assignee: Colgate-Palmolive Company, New York, NY (US)

( * ) Notice: Subject to any disclaimer, the term of this patent is extended or adjusted under 35 U.S.C. 154(b) by 208 days.

(21) Appl. No.: 13/884,040

(22) PCT Filed: Nov. 12, 2010

(86) PCT No.: PCT/US2010/056511

§ 371 (c)(1), (2), (4) Date: May 8, 2013

(87) PCT Pub. No.: WO2012/064338

PCT Pub. Date: May 18, 2012

(65) Prior Publication Data

US 2013/0224126 A1 Aug. 29, 2013

(51) Int. Cl.
*A61K 8/49* (2006.01)
*A61Q 11/00* (2006.01)
*A61K 8/34* (2006.01)
*A61K 8/44* (2006.01)

(52) U.S. Cl.
CPC ... *A61K 8/49* (2013.01); *A61K 8/34* (2013.01); *A61K 8/347* (2013.01); *A61K 8/44* (2013.01); *A61Q 11/00* (2013.01)

(58) Field of Classification Search
None
See application file for complete search history.

(56) References Cited

U.S. PATENT DOCUMENTS 3,535,421 A 10/1970 Briner et al.
3,678,154 A 7/1972 Widder et al.
3,696,191 A 10/1972 Weeks
3,991,177 A 11/1976 Vidra et al.
4,058,595 A 11/1977 Colodney
4,154,815 A 5/1979 Pader
4,355,022 A 10/1982 Rabussay
4,759,925 A * 7/1988 Gaffar .................... A61K 8/70 424/52
4,842,847 A 6/1989 Amjad
4,866,161 A 9/1989 Sikes et al.
4,885,155 A 12/1989 Parran, Jr. et al.
4,992,420 A 2/1991 Neeser
5,000,939 A 3/1991 Dring et al.
5,589,159 A 12/1996 Markowitz et al.
5,603,922 A * 2/1997 Winston .................. A61K 8/19 222/129
5,817,295 A * 10/1998 Chaudhari et al. ............. 424/49
6,696,072 B1 2/2004 Podolski
2002/0010300 A1* 1/2002 Mimoun ........................ 528/10
2007/0020342 A1* 1/2007 Modak et al. ................ 424/642
2007/0237737 A1* 10/2007 Dann et al. ...................... 424/74
2009/0035229 A1 2/2009 Eirew
2009/0042986 A1 2/2009 Hatanaka et al.
2009/0202450 A1 8/2009 Prencipe et al.
2010/0003353 A1 1/2010 Stephens et al.
2010/0286218 A1 11/2010 Berg et al.
2013/0064779 A1 3/2013 Yamane et al.

FOREIGN PATENT DOCUMENTS

JP 2006-137735 6/2006
JP 2008-512387 4/2008
RU 2116781 8/1998
SU 1303162 4/1987
TW 200934523 8/2009
WO WO 03/053430 7/2003
WO WO 04/000245 12/2003
WO WO 2006/029213 3/2006
WO WO 2009/099450 3/2008
WO WO 2008/109167 9/2008
WO WO 2009/099453 8/2009
WO WO 2009/099454 8/2009
WO WO 2009/100263 8/2009
WO WO 2009099454 A1 * 8/2009
WO WO 2010/019587 2/2010

OTHER PUBLICATIONS

MSDS for Kathon CG from Dow Chemical, downloaded Nov. 3, 2014 from the site: http://msdssearch.dow.com/PublishedLiteratureDOWCOM/dh_088a/0901b8038088a0e5.pdf?filepath=biocides/pdfs/noreg/253-02698.pdf&fromPage=GetDoc.*
Definition of "mouthwash" downloaded May 15, 2015 from http://www.merriam-webster.com/dictionary/mouthwash.*
Handbook of Pharm. Excipients, 6th Ed., 1986, pp. 64-65, 488-489.
Product information; Neolone PE—Technical Data Sheet. 2009, Retrieved from http://www.pdfio.com/k-569470.html#download_area on Aug. 6, 2014.
FEDOTOV, 2007, "Immunization," Great Dictionary of Medical Terms, p. 340.
International Search Report and Written Opinion in International Application No. PCT/US10/056511, mailed Oct. 20, 2011.
Reeder et al., 1978, "Dentin Permeability: Determinants of Hydraulic Conductance," J. Dental Research 57(2):187-193.
Wikipedia, 2012 "Orange Juice," from en.wikipedia.org/wiki/Orange_juice, retrieved from internet Jul. 12, 2012, pp. 1-5.
Written Opinion in International Application No. PCT/US10/056511, mailed Dec. 12, 2012.

* cited by examiner

*Primary Examiner* — Frederick Krass
*Assistant Examiner* — Michael P Cohen

(57) ABSTRACT

This invention relates to a mouthwash comprising an aqueous solution of an effective amount of a basic amino acid, in free or salt form together with an effective amount of a preservative selected from methylisothiazolinone (MIT), benzyl alcohol, phenoxyethanol, and combinations thereof; as well as to methods of using and of making such compositions.

8 Claims, No Drawings

ORAL CARE PRODUCT AND METHODS OF USE AND MANUFACTURE THEREOF

FIELD OF THE INVENTION

This invention relates to a mouthwash comprising a basic amino acid in free or salt form and a preservative selected from methylisothiazolinone, benzyl alcohol, phenoxyethanol, and combinations thereof, as well as to methods of using and of making these compositions.

BACKGROUND OF THE INVENTION

Because of their high water content, mouthwashes present particular challenges in preventing microbial contamination. Arginine and other basic amino acids have been proposed for use in oral care and are believed to have significant benefits in combating cavity formation and tooth sensitivity, but formulation in a mouthwash presents special challenges as mouthwashes comprising arginine or basic amino acids tend to have a basic pH, increasing potential for microbial contamination compared to acidic formulations. Moreover, not all preservatives are active at higher pH. Some preservatives negatively affect the taste or aesthetics of the product. While certain preservatives, such as ethanol or parabens, are known to effective at a range of pHs, these preservatives are not suitable for all products or all markets.

Accordingly, there is a need for improved preservative agents for use in mouthwashes comprising basic amino acids.

BRIEF SUMMARY OF THE INVENTION

It is now surprisingly discovered that mouthwashes comprising a basic amino acid such as arginine, in free or salt form, and a preservative selected from methylisothiazolinone, benzyl alcohol, phenoxyethanol, and combinations thereof, are stable and effective.

In one embodiment the mouthwash further comprises an anionic polymer and/or pyrophosphates.

The invention thus encompasses oral care compositions and methods of using the same that are effective in inhibiting or reducing the accumulation of plaque, reducing levels of acid producing (cariogenic) bacteria, remineralizing teeth, and inhibiting or reducing gingivitis. The invention also encompasses compositions and methods to clean the oral cavity and provide improved methods of promoting oral health and/or systemic health, including cardiovascular health, e.g., by reducing potential for systemic infection via the oral tissues.

The invention thus provides a mouthwash composition (a Composition of the Invention), comprising an aqueous solution of i. an effective amount of a basic amino acid, in free or salt form, e.g., arginine;
ii. an effective amount of a preservative selected from methylisothiazolinone (MIT), benzyl alcohol, phenoxyethanol, and combinations thereof.

The Compositions of the Invention may comprise additional ingredients, e.g., selected from one or more of water, surfactants, solvents, vitamins, minerals, polymers, enzymes, humectants, thickeners, additional antimicrobial agents, additional preservatives, flavorings, colorings and/or combinations thereof. In particular embodiments, the invention may comprise an anti-calculus agent for example a polyphosphate, e.g., pyrophosphate, tripolyphosphate, or hexametaphosphate, e.g., in alkali, e.g., sodium or potassium salt form, and/or may comprise a synthetic anionic polymeric polycarboxylate, such as 1:4 to 4:1 copolymers of maleic anhydride or acid with another polymerizable ethylenically unsaturated monomer, for example a copolymer of methyl vinyl ether/maleic anhydride.

Effective amounts for the preservatives in the Compositions of the Invention, separately or in combination, are, for example, as follows: MIT: less than 0.05%, e.g., 0.0005-0.03%, e.g. 0.001 to 0.01%, benzyl alcohol: less than 0.5%, e.g., 0.05-0.25%, e.g. 0.1%; or phenoxyethanol: less than 1%, e.g., 0.1-0.7%.

The invention further encompasses methods comprising applying compositions effective upon application to the oral cavity, e.g., rinsing the oral cavity, optionally in conjunction with brushing, to (i) reduce or inhibit formation of dental caries, (ii) reduce, repair or inhibit pre-carious lesions of the enamel, e.g., as detected by quantitative light-induced fluorescence (QLF) or electrical caries measurement (ECM), (iii) reduce or inhibit demineralization and promote remineralization of the teeth, (iv) reduce hypersensitivity of the teeth, (v) reduce or inhibit gingivitis, (vi) promote healing of sores or cuts in the mouth, (vii) reduce levels of acid producing bacteria, (viii) to increase relative levels of arginolytic bacteria, (ix) inhibit microbial biofilm formation in the oral cavity, (x) raise and/or maintain plaque pH at levels of at least pH 5.5 following sugar challenge, (xi) reduce plaque accumulation, (xii) treat, relieve or reduce dry mouth, (xiii) clean the teeth and oral cavity (xiv) reduce erosion, (xv) whiten teeth, (xvi) immunize the teeth against cariogenic bacteria; and/or (xvii) promote systemic health, including cardiovascular health, e.g., by reducing potential for systemic infection via the oral tissues.

DETAILED DESCRIPTION OF THE INVENTION

The invention thus provides, in a first embodiment, a mouthwash (Composition 1.0) comprising an aqueous solution of i. an effective amount of a basic amino acid, in free or salt form;
ii. an effective amount of a preservative selected from methylisothiazolinone (MIT), benzyl alcohol, phenoxyethanol, and combinations thereof;

for example, any of the following compositions:

1.0.1. Composition 1.0 wherein the basic amino acid is arginine, lysine, serine, citrullene, ornithine, creatine, histidine, diaminobutanoic acid, diaminoproprionic acid, salts thereof and/or combinations thereof.
1.0.2. Composition 1.0 or 1.0.1 wherein the basic amino acid has the L-configuration.
1.0.3. Any of the preceding compositions is provided in the form of a di- or tri-peptide comprising the basic amino acid, or salts thereof.
1.0.4. Any of the preceding compositions wherein the basic amino acid is arginine.
1.0.5. Any of the preceding compositions wherein the basic amino acid is L-arginine.
1.0.6. Any of the preceding compositions wherein the basic amino acid is partially or wholly in salt form.
1.0.7. Composition 1.0.6 wherein the basic amino acid is arginine phosphate.
1.0.8. Composition 1.0.6 wherein the basic amino acid is arginine hydrochloride.
1.0.9. Composition 1.0.6 wherein the basic amino acid is arginine bicarbonate.
1.0.10. Any of the preceding compositions wherein the basic amino acid is ionized by neutralization with an acid or a salt of an acid.

1.0.11. Any of the preceding compositions wherein the basic amino acid is present in an amount corresponding to 0.01 to 2%, e.g., 0.1 wt. % to 1 wt. % of the total composition weight, e.g., 0.8%, the weight of the basic amino acid being calculated as free base form.

1.0.12. Any of the foregoing compositions wherein the preservatives are present in amounts as follows:

i. MIT: less than 0.05%, e.g., 0.0005-0.03%, e.g. 0.001 to 0.01%;

ii. benzyl alcohol: less than 0.5%, e.g., 0.05-0.25%, e.g. 0.1%; and/or iii. phenoxyethanol: less than 1%, e.g., 0.1-0.7%.

1.0.13. Any of the foregoing compositions wherein the preservatives comprise a combination of MIT and benzyl alcohol.

1.0.14. The foregoing composition wherein the preservative comprises 0.01% MIT and 0.1% benzyl alcohol, or wherein the preservative comprises 0.001% MIT and 0.1% benzyl alcohol.

1.0.15. Any of the foregoing compositions further comprising an anti-calculus agent for example polyphosphate, e.g., pyrophosphate, tripolyphosphate, or hexametaphosphate, e.g., in salt form, e.g., sodium or potassium salt form, e.g., in an amount of from 0.1-3%.

1.0.16. The foregoing composition wherein the anti-calculus agent is a pyrophosphate selected from tetrasodium pyrophosphate and tetrapotassium pyrophosphate and mixtures thereof, e.g., in an amount sufficient to provide at least 1 wt. % pyrophosphate ions, 1-3 wt. %.

1.0.17. The foregoing composition comprising 0.1 to 1% tetrasodium pyrophosphate and 1-2% tetrapotassium pyrophosphate, e.g. 0.25-0.75% tetrasodium pyrophosphate and 1.0-1.5% tetrapotassium pyrophosphate.

1.0.18. Any of the preceding compositions comprising a polymer, e.g., at least one polymer selected from polyethylene glycols; synthetic anionic polymeric polycarboxylate, such as polyvinylmethyl ether maleic acid copolymers; polysaccharides (e.g., cellulose derivatives, for example carboxymethyl cellulose or polysaccharide gums, for example xanthan gum, gelluan gum or carrageenan gum); acrylates and combinations thereof.

1.0.19. Any of the foregoing compositions comprising a synthetic anionic polymeric polycarboxylate, e.g., in an amount of 1-10%, e.g., 2.5-7.5%.

1.0.20. The foregoing composition wherein the synthetic anionic polymeric polycarboxylate is a 1:4 to 4:1 copolymer of maleic anhydride or acid with another polymerizable ethylenically unsaturated monomer, e.g. methyl vinyl ether/maleic anhydride having a molecular weight (M.W.) of 30,000 to 5,000,000 daltons, for example 500 kD-3000 kD.

1.0.21. The foregoing composition comprising a co-polymer of methyl vinyl ether/maleic anhydride having the general structure $\text{-}[CH_2\text{—}CH(OCH_3)\text{—}CH(COOH)\text{—}CH(COOH)]_n\text{-}$.

1.0.22. The foregoing composition having a viscosity of CP at 25° C. of 1-3 kCP, e.g., $1.7\times10^3$ CP, and nominal molecular weight of 500 kD-3000 kD, e.g., $1.98\times10^6$, for example in an amount by weight of 1-10%, e.g., 5%

1.0.23. Any of the foregoing compositions wherein the composition is ethanol-free.

1.0.24. Any of the foregoing compositions further comprising a soluble calcium salt, e.g., selected from calcium glycerophosphate and salts of soluble carboxylic acids, and mixtures thereof, e.g., wherein the calcium salt is selected from calcium citrate, calcium malate, calcium lactate, calcium formate, calcium fumarate, calcium gluconate, calcium lactate gluconate, calcium aspartate, and calcium propionate, and mixtures thereof.

1.0.25. Any of the preceding compositions further comprising a fluoride source, e.g., a fluoride salt, for example sodium fluoride, or wherein the fluoride is covalently bound to another atom, e.g., a monofluorophosphate, for example sodium monofluorophosphate, a fluorosilicate, e.g., sodium fluorosilicate or ammonium fluorosilicate, or a fluorosulfate, e.g., hexafluorosulfate, amine fluoride and combinations thereof.

1.0.26. The preceding composition wherein the fluoride salt is present in an amount to provide 100 to 250 ppm available fluoride.

1.0.27. Any of the preceding compositions comprising sodium fluoride in an amount of 0.01-0.1%, e.g., 0.05%.

1.0.28. Any of the preceding compositions wherein the pH is between 7 and 9, e.g., 8 to 8.5, e.g., 8.3.

1.0.29. Any of the preceding compositions wherein the pH is adjusted, e.g, using a weak organic acid, for example citric acid.

1.0.30. Any of the preceding compositions further comprising an abrasive or particulate.

1.0.31. Any of the preceding compositions comprising a non-ionic surfactant, e.g., in an amount of from 0.5 -5%, for example 1-2%, selected from polaxamers (e.g., polaxamer 407), polysorbates (e.g., polysorbate 20), polyoxyl hydrogenated castor oil (e.g., polyoxyl 40 hydrogenated castor oil), and mixtures thereof.

1.0.32. Any of the preceding compositions comprising at least one humectant.

1.0.33. Any of the preceding compositions comprising at least one humectant selected from glycerin, sorbitol, propylene glycol, and combinations thereof, e.g., in a total amount of 10-40%.

1.0.34. Any of the preceding compositions comprising polymer films.

1.0.35. Any of the preceding compositions comprising flavoring, fragrance and/or coloring.

1.0.36. Any of the preceding compositions comprising at least 50% water.

1.0.37. Any of the preceding compositions comprising an additional antibacterial agent selected from halogenated diphenyl ether (e.g. triclosan), herbal extracts and essential oils (e.g., rosemary extract, tea extract, magnolia extract, thymol, menthol, eucalyptol, geraniol, carvacrol, citral, hinokitol, catechol, methyl salicylate, epigallocatechin gallate, epigallocatechin, gallic acid, miswak extract, sea-buckthorn extract), bisguanide antiseptics (e.g., chlorhexidine, alexidine or octenidine), quaternary ammonium compounds (e.g., cetylpyridinium chloride (CPC), benzalkonium chloride, tetradecylpyridinium chloride (TPC), N-tetradecyl-4-ethylpyridinium chloride (TDEPC)), phenolic antiseptics, hexetidine, octenidine, sanguinarine, povidone iodine, delmopinol, salifluor, metal ions (e.g., zinc salts, for example, zinc citrate, stannous salts, copper salts, iron salts), sanguinarine, propolis and oxygenating agents (e.g., hydrogen peroxide, buffered sodium peroxyborate or peroxycarbonate), phthalic acid and its salts, monoperthalic acid and its salts and esters, ascorbyl stearate, oleoyl sarcosine, alkyl sulfate, dioctyl sulfosuccinate, salicylanilide, domiphen bromide, delmopinol, octapinol and other piperidino derivatives, nicin preparations, chlorite salts; and mixtures of any of the foregoing.

1.0.38. Any of the preceding compositions comprising an antioxidant, e.g., selected from the group consisting of Co-enzyme Q10, PQQ, Vitamin C, Vitamin E, Vitamin A, BHT, anethole-dithiothione, and mixtures thereof.

1.0.39. Any of the preceding compositions comprising a whitening agent.

1.0.40. Any of the preceding compositions comprising a whitening agent selected from a whitening active selected from the group consisting of peroxides, metal chlorites, perborates, percarbonates, peroxyacids, hypochlorites, and combinations thereof.

1.0.41. Any of the preceding compositions further comprising hydrogen peroxide or a hydrogen peroxide source, e.g., urea peroxide or a peroxide salt or complex (e.g., such as peroxyphosphate, peroxycarbonate, perborate, peroxysilicate, or persulphate salts; for example calcium peroxyphosphate, sodium perborate, sodium carbonate peroxide, sodium peroxyphosphate, and potassium persulfate), or hydrogen peroxide polymer complexes such as hydrogen peroxide-polyvinyl pyrrolidone polymer complexes.

1.0.42. Any of the preceding compositions further comprising an agent that interferes with or prevents bacterial attachment, e.g., ELA or chitosan.

1.0.43. Any of the preceding compositions further comprising a physiologically acceptable potassium salt, e.g., potassium nitrate or potassium chloride, in an amount effective to reduce dentinal sensitivity.

1.0.44. Any of the preceding compositions comprising from 0.01% to 1% of a physiologically acceptable potassium salt, e.g., potassium nitrate and/or potassium chloride.

1.0.45. Any of the preceding compositions effective upon application to the oral cavity, e.g., by rinsing, optionally in conjunction with brushing, to (i) reduce or inhibit formation of dental caries, (ii) reduce, repair or inhibit pre-carious lesions of the enamel, e.g., as detected by quantitative light-induced fluorescence (QLF) or electrical caries measurement (ECM), (iii) reduce or inhibit demineralization and promote remineralization of the teeth, (iv) reduce hypersensitivity of the teeth, (v) reduce or inhibit gingivitis, (vi) promote healing of sores or cuts in the mouth, (vii) reduce levels of acid producing bacteria, (viii) to increase relative levels of arginolytic bacteria, (ix) inhibit microbial biofilm formation in the oral cavity, (x) raise and/or maintain plaque pH at levels of at least pH 5.5 following sugar challenge, (xi) reduce plaque accumulation, (xii) treat, relieve or reduce dry mouth, (xiii) clean the teeth and oral cavity (xiv) reduce erosion, (xv) prevents stains and/or whiten teeth, (xvi) immunize the teeth against cariogenic bacteria; and/or (xvii) promote systemic health, including cardiovascular health, e.g., by reducing potential for systemic infection via the oral tissues.

1.0.46. A composition obtained or obtainable by combining the ingredients as set forth in any of the preceding compositions.

Levels of active ingredients will vary based on the nature of the delivery system and the particular active. For example, the basic amino acid may be present at levels from, e.g., 0.1 to 5 wt % (expressed as weight of free base), e.g., 0.1 to 3 wt %. Fluoride may be present at levels of, e.g., 25 to 250 ppm, or up to 10× higher for a professional or prescription treatment product. Levels of antibacterial will vary similarly, depending on the agent used. For example, a triclosan mouthrinse may contain, e.g., 0.03 wt % triclosan.

In another embodiment, the invention encompasses a method to improve oral health comprising applying an effective amount of the oral composition of any of the embodiments set forth above to the oral cavity of a subject in need thereof, e.g., a method to i. reduce or inhibit formation of dental caries, ii. reduce, repair or inhibit early enamel lesions, e.g., as detected by quantitative light-induced fluorescence (QLF) or electrical caries measurement (ECM), iii. reduce or inhibit demineralization and promote remineralization of the teeth, iv. reduce hypersensitivity of the teeth, v. reduce or inhibit gingivitis, vi. promote healing of sores or cuts in the mouth, vii. reduce levels of acid producing bacteria, viii. to increase relative levels of arginolytic bacteria, ix. inhibit microbial biofilm formation in the oral cavity, x. raise and/or maintain plaque pH at levels of at least pH 5.5 following sugar challenge, xi. reduce plaque accumulation, xii. treat dry mouth, xiii. enhance systemic health, including cardiovascular health, e.g., by reducing potential for systemic infection via the oral tissues, xiv. whiten teeth, xv. reduce erosion of the teeth, xvi. immunize (or protect) the teeth against cariogenic bacteria and their effects, and/or xvii. clean the teeth and oral cavity.

The invention further comprises the use of methylisothiazolinone, benzyl alcohol, phenoxyethanol, and combinations thereof in the manufacture of a Composition of the Invention, e.g., for use in any of the indications set forth in the above method.

Basic Amino Acids

The basic amino acids which can be used in the compositions and methods of the invention include not only naturally occurring basic amino acids, such as arginine, lysine, and histidine, but also any basic amino acids having a carboxyl group and an amino group in the molecule, which are water-soluble and provide an aqueous solution with a pH of 7 or greater.

Accordingly, basic amino acids include, but are not limited to, arginine, lysine, serine, citrullene, ornithine, creatine, histidine, diaminobutanoic acid, diaminoproprionic acid, salts thereof or combinations thereof. In a particular embodiment, the basic amino acids are selected from arginine, citrullene, and ornithine.

In certain embodiments, the basic amino acid is arginine, for example, L-arginine, or a salt thereof.

The compositions of the invention are intended for topical use in the mouth and so salts for use in the present invention should be safe for such use, in the amounts and concentrations provided. Suitable salts include salts known in the art to be pharmaceutically acceptable salts are generally considered to be physiologically acceptable in the amounts and concentrations provided. Physiologically acceptable salts include those derived from pharmaceutically acceptable inorganic or organic acids or bases, for example acid addition salts formed by acids which form a physiological acceptable anion, e.g., hydrochloride or bromide salt, and base addition salts formed by bases which form a physiologically acceptable cation, for example those derived from alkali metals such as potassium and sodium or alkaline earth metals such as calcium and magnesium. Physiologically acceptable salts may be obtained using standard procedures known in the art, for example, by reacting a sufficiently basic compound such as an amine with a suitable acid affording a physiologically acceptable anion.

Fluoride Ion Source: The oral care compositions may further include one or more fluoride ion sources, e.g., soluble fluoride salts. A wide variety of fluoride ion-yielding materials can be employed as sources of soluble fluoride in the present compositions. Examples of suitable fluoride ion-yielding materials are found in U.S. Pat. No. 3,535,421, to Briner et al.; U.S. Pat. No. 4,885,155, to Parran, Jr. et al. and U.S. Pat. No. 3,678,154, to Widder et al., incorporated herein by reference. Representative fluoride ion sources include, but are not limited to, stannous fluoride, sodium fluoride, potassium fluoride, sodium monofluorophosphate, sodium fluorosilicate, ammonium fluorosilicate, amine fluoride, ammonium fluoride, and combinations thereof. In certain embodiments the fluoride ion source includes stannous fluoride, sodium fluoride, sodium monofluorophosphate as well as mixtures thereof Where the formulation comprises calcium salts, the fluoride salts are preferably salts wherein the fluoride is covalently bound to another atom, e.g., as in sodium monofluorophosphate, rather than merely ionically bound, e.g., as in sodium fluoride.

Surfactants

The invention may in some embodiments contain anionic surfactants, for example, water-soluble salts of higher fatty acid monoglyceride monosulfates, such as the sodium salt of the monosulfated monoglyceride of hydrogenated coconut oil fatty acids such as sodium N-methyl N-cocoyl taurate, sodium cocomo-glyceride sulfate; higher alkyl sulfates, such as sodium lauryl sulfate; higher alkyl-ether sulfates, e.g., of formula $CH_3(CH_2)_mCH_2(OCH_2CH_2)_nOSO_3X$, wherein m is 6-16, e.g., 10, n is 1-6, e.g., 2, 3 or 4, and X is Na or K, for example sodium laureth-2 sulfate ($CH_3(CH_2)_{10}CH_2(OCH_2CH_2)_2OSO_3Na$); higher alkyl aryl sulfonates such as sodium dodecyl benzene sulfonate (sodium lauryl benzene sulfonate); higher alkyl sulfoacetates, such as sodium lauryl sulfoacetate (dodecyl sodium sulfoacetate), higher fatty acid esters of 1,2 dihydroxy propane sulfonate, sulfocolaurate (N-2-ethyl laurate potassium sulfoacetamide) and sodium lauryl sarcosinate. By "higher alkyl" is meant, e.g., $C_{6-30}$ alkyl. In particular embodiments, the anionic surfactant (where present) is selected from sodium lauryl sulfate and sodium ether lauryl sulfate. When present, the anionic surfactant is present in an amount which is effective, e.g., >0.001% by weight of the formulation, but not at a concentration which would be irritating to the oral tissue, e.g., 1%, and optimal concentrations depend on the particular formulation and the particular surfactant. In one embodiment, the anionic surfactant is present at from 0.03% to 0.5% by weight, e.g., 0.15%.

In another embodiment, cationic surfactants useful in the present invention can be broadly defined as derivatives of aliphatic quaternary ammonium compounds having one long alkyl chain containing 8 to 18 carbon atoms such as lauryl trimethylammonium chloride, cetyl pyridinium chloride, cetyl trimethylammonium bromide, di-isobutylphenoxyethyldimethylbenzylammonium chloride, coconut alkyltrimethylammonium nitrite, cetyl pyridinium fluoride, and mixtures thereof. Illustrative cationic surfactants are the quaternary ammonium fluorides described in U.S. Pat. No. 3,535,421, to Briner et al., herein incorporated by reference. Certain cationic surfactants can also act as germicides in the compositions.

Illustrative nonionic surfactants that can be used in the compositions of the invention can be broadly defined as compounds produced by the condensation of alkylene oxide groups (hydrophilic in nature) with an organic hydrophobic compound which may be aliphatic or alkylaromatic in nature. Examples of suitable nonionic surfactants include, but are not limited to, the Pluronics, polyethylene oxide condensates of alkyl phenols, products derived from the condensation of ethylene oxide with the reaction product of propylene oxide and ethylene diamine, ethylene oxide condensates of aliphatic alcohols, long chain tertiary amine oxides, long chain tertiary phosphine oxides, long chain dialkyl sulfoxides and mixtures of such materials. In a particular embodiment, the composition of the invention comprises a nonionic surfactant selected from polaxamers (e.g., polaxamer 407), polysorbates (e.g., polysorbate 20), polyoxyl hydrogenated castor oils (e.g., polyoxyl 40 hydrogenated castor oil), and mixtures thereof.

In certain embodiments, zwitterionic synthetic surfactants useful in the present invention can be broadly described as derivatives of aliphatic quaternary ammonium, phosphomium, and sulfonium compounds, in which the aliphatic radicals can be straight chain or branched, and wherein one of the aliphatic substituents contains 8 to 18 carbon atoms and one contains an anionic water-solubilizing group, e.g., carboxy, sulfonate, sulfate, phosphate or phosphonate.

Illustrative examples of the surfactants suited for inclusion into the composition include, but are not limited to, sodium alkyl sulfate, sodium lauroyl sarcosinate, cocoamidopropyl betaine and polysorbate 20, and combinations thereof.

The surfactant or mixtures of compatible surfactants can be present in the compositions of the present invention in 0.1% to 5%, in another embodiment 0.3% to 3% and in another embodiment 0.5% to 2% by weight of the total composition.

Flavoring Agents

The oral care compositions of the invention may also include a flavoring agent. Flavoring agents which are used in the practice of the present invention include, but are not limited to, essential oils and various flavoring aldehydes, esters, alcohols, and similar materials, as well as sweeteners such as sodium saccharin. Examples of the essential oils include oils of spearmint, peppermint, wintergreen, sassafras, clove, sage, eucalyptus, marjoram, cinnamon, lemon, lime, grapefruit, and orange. Also useful are such chemicals as menthol, carvone, and anethole. Certain embodiments employ the oils of peppermint and spearmint.

The flavoring agent is incorporated in the oral composition at a concentration of 0.01 to 1% by weight.

Chelating and Anti-Calculus Agents

The oral care compositions of the invention also may optionally include one or more chelating agents able to complex calcium found in the cell walls of the bacteria. Binding of this calcium weakens the bacterial cell wall and augments bacterial lysis.

Another group of agents suitable for use as chelating or anti-calculus agents in the present invention are the soluble pyrophosphates. The pyrophosphate salts used in the present compositions can be any of the alkali metal pyrophosphate salts. In certain embodiments, salts include tetra alkali metal pyrophosphate, dialkali metal diacid pyrophosphate, trialkali metal monoacid pyrophosphate and mixtures thereof, wherein the alkali metals are sodium or potassium. The salts are useful in both their hydrated and unhydrated forms. An effective amount of pyrophosphate salt useful in the present composition is generally enough to provide at least 0.5 wt. % pyrophosphate ions, 0.9-3 wt. %.

The pyrophosphates also contribute to preservation of the compositions by lowering water activity.

Polymers

The oral care compositions of the invention also optionally include one or more polymers, such as polyethylene glycols, polyvinylmethyl ether maleic acid copolymers, polysaccharides (e.g., cellulose derivatives, for example carboxymethyl cellulose, or polysaccharide gums, for example xanthan gum or carrageenan gum). Acidic polymers, for example polyacrylate gels, may be provided in the form of their free acids or partially or fully neutralized water soluble alkali metal (e.g., potassium and sodium) or ammonium salts.

In a particular embodiment, the compositions of the invention include synthetic anionic polymeric polycarboxylates, such as 1:4 to 4:1 copolymers of maleic anhydride or acid with another polymerizable ethylenically unsaturated monomer, preferably methyl vinyl ether/maleic anhydride having a molecular weight (M.W.) of 30,000 to 3,000,000, most preferably 30,000 to 800,000. These copolymers are available for example as Gantrez. e.g., AN 139 (M.W. 500,000), AN 119 (M.W. 250,000) and S-97 Pharmaceutical Grade (M.W. 700,000) available from ISP Technologies, Inc., Bound Brook, N.J. 08805. The enhancing agents when present are present in amounts of 1 to 10% by weight.

Other operative polymers include those such as the 1:1 copolymers of maleic anhydride with ethyl acrylate, hydroxyethyl methacrylate, N-vinyl-2-pyrollidone, or ethylene, the latter being available for example as Monsanto EMA No. 1103, M.W. 10,000 and EMA Grade 61, and 1:1 copolymers of acrylic acid with methyl or hydroxyethyl methacrylate, methyl or ethyl acrylate, isobutyl vinyl ether or N-vinyl-2-pyrrolidone.

Suitable generally, are polymerized olefinically or ethylenically unsaturated carboxylic acids containing an activated carbon-to-carbon olefinic double bond and at least one carboxyl group, that is, an acid containing an olefinic double bond which readily functions in polymerization because of its presence in the monomer molecule either in the alpha-beta position with respect to a carboxyl group or as part of a terminal methylene grouping. Illustrative of such acids are acrylic, methacrylic, ethacrylic, alpha-chloroacrylic, crotonic, beta-acryloxy propionic, sorbic, alpha-chlorsorbic, cinnamic, beta-styrylacrylic, muconic, itaconic, citraconic, mesaconic, glutaconic, aconitic, alpha-phenylacrylic, 2-benzyl acrylic, 2-cyclohexylacrylic, angelic, umbellic, fumaric, maleic acids and anhydrides. Other different olefinic monomers copolymerizable with such carboxylic monomers include vinylacetate, vinyl chloride, dimethyl maleate and the like. Copolymers contain sufficient carboxylic salt groups for water-solubility.

A further class of polymeric agents includes a composition containing homopolymers of substituted acrylamides and/or homopolymers of unsaturated sulfonic acids and salts thereof, in particular where polymers are based on unsaturated sulfonic acids selected from acrylamidoalykane sulfonic acids such as 2-acrylamide 2 methylpropane sulfonic acid having a molecular weight of 1,000 to 2,000,000, described in U.S. Pat. No. 4,842,847, Jun. 27, 1989 to Zahid, incorporated herein by reference.

Another useful class of polymeric agents includes polyamino acids, particularly those containing proportions of anionic surface-active amino acids such as aspartic acid, glutamic acid and phosphoserine, as disclosed in U.S. Pat. No. 4,866,161 Sikes et al., incorporated herein by reference.

In preparing oral care compositions, it is sometimes necessary to add some thickening material to provide a desirable consistency or to stabilize or enhance the performance of the formulation. In certain embodiments, the thickening agents are carboxyvinyl polymers, carrageenan, hydroxyethyl cellulose and water soluble salts of cellulose ethers such as sodium carboxymethyl cellulose and sodium carboxymethyl hydroxyethyl cellulose. Natural gums such as karaya, gum arabic, and gum tragacanth can also be incorporated. Colloidal magnesium aluminum silicate or finely divided silica can be used as component of the thickening composition to further improve the composition's texture. In certain embodiments, thickening agents in an amount of 0.5% to 5% by weight of the total composition are used.

Enzymes

The oral care compositions of the invention may also optionally include one or more enzymes. Useful enzymes include any of the available proteases, glucanohydrolases, endoglycosidases, amylases, mutanases, lipases and mucinases or compatible mixtures thereof. In certain embodiments, the enzyme is a protease, dextranase, endoglycosidase and mutanase. In another embodiment, the enzyme is papain, endoglycosidase or a mixture of dextranase and mutanase. Additional enzymes suitable for use in the present invention are disclosed in U.S. Pat. No. 5,000,939 to Dring et al., U.S. Pat. Nos. 4,992,420; 4,355,022; 4,154,815; 4,058,595; 3,991,177; and 3,696,191 all incorporated herein by reference. An enzyme of a mixture of several compatible enzymes in the current invention constitutes 0.002% to 2.0% in one embodiment or 0.05% to 1.5% in another embodiment or in yet another embodiment 0.1% to 0.5%.

Water

Water is present in the oral compositions of the invention. Water, employed in the preparation of commercial oral compositions should be deionized and free of organic impurities. Water commonly makes up the balance of the compositions and includes 10% to 90%, e.g., 40% to 70% by weight of the oral compositions. This amount of water includes the free water which is added plus that amount which is introduced with other materials such as with sorbitol or any components of the invention.

Humectants

Within certain embodiments of the oral compositions, it is also desirable to incorporate a humectant to reduce evaporation and also contribute towards preservation by lowering water activity. Certain humectants can also impart desirable sweetness or flavor to the compositions. The humectant, on a pure humectant basis, generally includes 15% to 70% in one embodiment or 30% to 65% in another embodiment by weight of the composition.

Suitable humectants include edible polyhydric alcohols such as glycerine, sorbitol, xylitol, propylene glycol as well as other polyols and mixtures of these humectants. Mixtures of glycerine and sorbitol may be used in certain embodiments as the humectant component of the compositions herein.

The present invention in its method aspect involves applying to the oral cavity a safe and effective amount of the compositions described herein.

The compositions and methods according to the invention are useful to a method to protect the teeth by facilitating repair and remineralization, in particular to reduce or inhibit formation of dental caries, reduce or inhibit demineralization and promote remineralization of the teeth, reduce hypersensitivity of the teeth, and reduce, repair or inhibit early enamel lesions, e.g., as detected by quantitative light-induced fluorescence (QLF) or electronic caries monitor (ECM).

Quantitative Light-induced Fluorescence is a visible light fluorescence that can detect early lesions and longitudinally monitor the progression or regression. Normal teeth fluoresce in visible light; demineralized teeth do not or do so only to a lesser degree. The area of demineralization can be quantified and its progress monitored. Blue laser light is used to make the teeth auto fluoresce. Areas that have lost mineral have lower fluorescence and appear darker in comparison to a sound tooth surface. Software is used to quantify the fluorescence from a white spot or the area/volume associated with the lesion. Generally, subjects with existing white spot lesions are recruited as panelists. The measurements are performed in vivo with real teeth. The lesion area/volume is measured at the beginning of the clinical. The reduction (improvement) in lesion area/volume is measured at the end of 6 months of product use. The data is often reported as a percent improvement versus baseline.

Electrical Caries Monitoring is a technique used to measure mineral content of the tooth based on electrical resistance. Electrical conductance measurement exploits the fact that the fluid-filled tubules exposed upon demineralization and erosion of the enamel conduct electricity. As a tooth loses mineral, it becomes less resistive to electrical current due to increased porosity. An increase in the conductance of the patient's teeth therefore may indicate demineralization. Generally, studies are conducted of root surfaces with an existing lesion. The measurements are performed in vivo with real teeth. Changes in electrical resistance before and after 6 month treatments are made. In addition, a classical caries score for root surfaces is made using a tactile probe. The hardness is classified on a three point scale: hard, leathery, or soft. In this type of study, typically the results are reported as electrical resistance (higher number is better) for the ECM measurements and an improvement in hardness of the lesion based on the tactile probe score.

Test methods for the desensitizing properties of the compositions described herein, uses the method described in U.S. Pat. No. 5,589,159, the disclosure of which is incorporated by reference herein in its entirety. This method measures the hydraulic conductance of materials, providing an objective reduction in fluid flow that correlates with reduction in fluid flow in dentinal tubules. In this method, intact human molars free from caries and restorations are sectioned perpendicularly to the long axis of the tooth with a metallurgical saw to form thin sections, or discs, from about 0.4 to about 0.8 mm thick. Sections containing dentin and free of enamel were selected for testing and then etched with citric acid solution to remove the smear layer. Each disc was mounted into a split chambered device described in J. Dent. Research, 57:187 (1978) which is a special leak-proof chamber connected to a pressurized fluid reservoir containing a tissue culture fluid. By using a mixture of pressurized nitrogen and carbon dioxide gas, the fluid can be made at physiological pH. To further ensure accuracy, the discs were wetted with artificial saliva (phosphate buffer saline , PBS) to approximate intra-oral conditions. The apparatus includes a glass capillary tube attached to a flow sensor (FLODEC, DeMarco Engineering SA, Geneva). An air bubble is injected into the glass capillary tube. By measuring the displacement of the bubble as a function of time, fluid flow through the dentin disc can be measured. Fluid flow is equivalent to the dentin permeability.

The Compositions of the Invention are thus useful in a method to reduce early lesions of the enamel (as measured by QLF or ECM) relative to a composition lacking effective amounts of fluorine and/or arginine.

The Compositions of the invention are additionally useful in methods to reduce harmful bacteria in the oral cavity, for example methods to reduce or inhibit gingivitis, reduce levels of acid producing bacteria, to increase relative levels of arginolytic bacteria, inhibit microbial biofilm formation in the oral cavity, raise and/or maintain plaque pH at levels of at least pH 5.5 following sugar challenge, reduce plaque accumulation, and/or clean the teeth and oral cavity.

Finally, by increasing the pH in the mouth and discouraging pathogenic bacteria, the Compositions of the Invention are useful to promote healing of sores or cuts in the mouth.

The compositions and methods according to the invention can be incorporated into oral compositions for the care of the mouth and teeth such as toothpastes, transparent pastes, gels, mouth rinses, sprays and chewing gum.

Enhancing oral health also provides benefits in systemic health, as the oral tissues can be gateways for systemic infections. Good oral health is associated with systemic health, including cardiovascular health. The compositions and methods of the invention provide particular benefits because basic amino acids, especially arginine, are sources of nitrogen which supply NO synthesis pathways and thus enhance microcirculation in the oral tissues. Providing a less acidic oral environment is also helpful in reducing gastric distress and creates an environment less favorable to Heliobacter, which is associated with gastric ulcers. Arginine in particular is required for high expression of specific immune cell receptors, for example T-cell receptors, so that arginine can enhance an effective immune response. The compositions and methods of the invention are thus useful to enhance systemic health, including cardiovascular health.

As used throughout, ranges are used as shorthand for describing each and every value that is within the range. Any value within the range can be selected as the terminus of the range. In addition, all references cited herein are hereby incorporated by reference in their entireties. In the event of a conflict in a definition in the present disclosure and that of a cited reference, the present disclosure controls. It is understood that when formulations are described, they may be described in terms of their ingredients, as is common in the art, notwithstanding that these ingredients may react with one another in the actual formulation as it is made, stored and used, and such products are intended to be covered by the formulations described.

The following examples further describe and demonstrate illustrative embodiments within the scope of the present invention. The examples are given solely for illustration and are not to be construed as limitations of this invention as many variations are possible without departing from the spirit and scope thereof. Various modifications of the invention in addition to those shown and described herein should be apparent to those skilled in the art and are intended to fall within the appended claims.

EXAMPLE 1

Mouthwashes

Formulations of the invention are prepared with the following ingredients:

| RAW MATERIAL | WEIGHT % |
|---|---|
| Sorbitol (70% solution) | 7 |
| Glycerin | 18 |
| Propylene glycol | 4 |
| L-arginine | 0.8 |
| Gantrez S-97 (13% Solution) | 5 |
| Pyrophosphate salts | 1.7 |
| Sodium fluoride | 0.05 |
| Sodium saccharin | 0.02 |
| Citric acid (anhydrous) | 0.02 |
| Surfactants | 1.7 |
| Flavor | 0.23 |
| Dye | 0.0002 |
| Benzyl alcohol | 0.1 |
| Methylisothiazolinone (MIT) | 0.01 |
| Water | Balance |
| TOTAL | 100 |
| pH | 8.3 |
| Water activity: | <94% |

To optimize the preservative system, the preservatives benzyl alcohol and methylisothiazolinone (MIT) are substituted with different preservatives in the above formulation, and the characteristics of the formulation tested for antimicrobial efficacy, flavor impact, and aesthetics impact.

The Antimicrobial Preservation Effectiveness Test is used to determine the antimicrobial preservation effectiveness of water-based product formulations by means of a double challenge test. Products are developed to withstand microbial challenges introduced by normal consumer use. The test is run on an aged sample (13 weeks, 40° C.). The test uses two pools of microorganisms: bacteria/yeast and mold. The product is challenged at a 1% level at day 0 and at day 7. Reduction of the inoculum is monitored over a 28 day period. The following are the acceptance criteria for mouth wash formulas.

Bacteria and yeast must show a 99.9% reduction (3 logs) of the bacterial inoculum as determined by plate count on day 7 following each inoculation. No increase after day 7 of the second inoculation and for the remainder of the test within normal variation of the data.

Mold must show a 90.0% reduction (1 log) of the mold inoculum as determined by the plate count on day 14 following the second inoculation (day 21). No increase from day 14 to day 21 of the second inoculation of the test within normal variation of the data.

Flavor is evaluated via an organoleptic evaluation by trained flavorists.

Aesthetics are evaluated by a visual comparison to a control sample having the same types and levels of colorant and flavoring agents.

Results of the comparative testing are as follows, where a "√" indicates criteria were met, and an "X" indicates criteria were not met.

| | Preservative | | | | |
|---|---|---|---|---|---|
| | KSorbate | MIT | Benzyl alcohol | Phenoxyethanol | Polyamidopropyl Bisguanide |
| Micro robustness | X | ✓ | ✓ | ✓ | X |
| In vitro eff. | ✓ | ✓ | ✓ | ✓ | ✓ |
| Flavor impact | X | 0.001% ✓<br>0.01% X | slight | X | X |
| Aesthetics impact | ✓ | ✓ | ✓ | ✓ | X |

| | Preservative | | | | |
|---|---|---|---|---|---|
| | Zinc Oxide | MIT/benzyl alcohol | MIT/Phenoxy-ethanol | MIT/Benzyl alc/ Phenoxyethanol | Zinc Ox/MIT |
| Micro robustness | X | ✓ | ✓ | ✓ | X |
| In vitro eff. | ✓ | ✓ | ✓ | ✓ | ✓ |
| Flavor impact | X | ✓ | X | X | ✓ |
| Aesthetics impact | ✓ | ✓ | ✓ | ✓ | ✓ |

These results show that the different preservative systems behave unpredictably in the mouthwash formulations. The only preservatives which provided acceptable microbial control are benzyl alcohol, methylisothiazolinone (MIT), and phenoxyethanol, separately or in combination. Benzyl alcohol and methylisothiazolinone (MIT) are preferred as phenoxyethanol has a negative impact on flavor, although this impact can be largely masked by optimization of the flavoring.

What is claimed is:

1. A mouthwash composition comprising an aqueous solution of a. an effective amount of arginine, in free or salt form, wherein the basic amino acid is present in an amount corresponding to 0.01 to 2 wt % of the total composition weight, the weight of the basic amino acid being calculated as free base form;

b. an effective amount of a preservative selected from methylisothiazolinone (MIT), benzyl alcohol, phenoxyethanol, and combinations thereof, wherein the preservatives are present, separately or in combination, in amounts as follows:

i. MIT: 0.0005-0.03 wt. %;

ii. Benzyl alcohol: 0.05-0.25 wt. % iii. Phenoxyethanol: 0.1-0.7 wt. %;

wherein the composition is a mouthwash.

2. The composition according to claim 1 further comprising a pyrophosphate.

3. The composition according to claim 1 further comprising a synthetic anionic polymeric polycarboxylate.

4. The composition according to claim 1 further comprising a fluoride ion source.

5. The composition according to claim 1 wherein the mouthwash is ethanol-free.

6. The composition according to claim 1 further comprising one or more of humectants, flavorings, and surfactants.

7. The composition according to claim 1 wherein the preservative comprises an amount effective to provide microbial control.

8. A method to improve oral health comprising applying an effective amount of the composition of any of the preceding claims to the oral cavity of a subject in need thereof to a. reduce or inhibit formation of dental caries, b. reduce, repair or inhibit early enamel lesions, c. reduce or inhibit demineralization and promote remineralization of the teeth, d. reduce hypersensitivity of the teeth, e. reduce or inhibit gingivitis, f. promote healing of sores or cuts in the mouth, g. reduce levels of acid producing bacteria, h. to increase relative levels of arginolytic bacteria, i. inhibit microbial biofilm formation in the oral cavity, j. raise and/or maintain plaque pH at levels of at least pH 5.5 following sugar challenge, k. reduce plaque accumulation, l. treat, relieve or reduce dry mouth, m. whiten teeth, n. enhance systemic health, including cardiovascular health, o. reduce erosion of the teeth, p. to immunize the teeth against cariogenic bacteria and their effects, and/or q. clean the teeth and oral cavity.

* * * * *